(12) United States Patent
Altmann (10) Patent No.: US 11,583,249 B2
(45) Date of Patent: Feb. 21, 2023

(54) METHOD AND APPARATUS FOR PERFORMING NON-FLUOROSCOPIC TRANSSEPTAL PROCEDURE

(71) Applicant: Biosense Webster (Israel) Ltd., Yokneam (IL)

(72) Inventor: Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 595 days.

(21) Appl. No.: 15/698,758

(22) Filed: Sep. 8, 2017

(65) Prior Publication Data
US 2019/0076117 A1     Mar. 14, 2019

(51) Int. Cl.
*A61B 8/00*     (2006.01)
*A61B 17/34*     (2006.01)
(Continued)

(52) U.S. Cl.
CPC .......... *A61B 8/4245* (2013.01); *A61B 8/0858* (2013.01); *A61B 8/0883* (2013.01); *A61B 8/12* (2013.01); *A61B 8/445* (2013.01); *A61B 8/4494* (2013.01); *A61B 8/565* (2013.01); *A61B 17/3478* (2013.01); *A61B 34/20* (2016.02); *A61B 90/37* (2016.02); *A61B 5/287* (2021.01); *A61B 8/4483* (2013.01); *A61B 18/1492* (2013.01); *A61B 2017/00247* (2013.01); *A61B 2017/3413* (2013.01); *A61B 2018/00351* (2013.01); *A61B 2018/00577* (2013.01);
(Continued)

(58) Field of Classification Search
CPC .................................................. A61B 8/4245
See application file for complete search history.

(56) References Cited

U.S. PATENT DOCUMENTS

| | | |
|---|---|---|
| 5,076,278 A | 12/1991 | Vilkomerson et al. |
| 5,088,500 A | 2/1992 | Wedel et al. |

(Continued)

FOREIGN PATENT DOCUMENTS

| | | |
|---|---|---|
| JP | 05-337127 A | 12/1993 |
| WO | 2015/091409 A1 | 6/2015 |

OTHER PUBLICATIONS

International Search Report and Written Opinion dated Jan. 4, 2019 for PCT International Application No. PCT/IB2018/056694.
(Continued)

*Primary Examiner* — Joel F Brutus
(74) *Attorney, Agent, or Firm* — Volpe Koenig (57) ABSTRACT

A system and method for performing a non-fluoroscopic transseptal procedure may comprise a catheter and a device comprising a sheath, an introducer and a transducer embedded on the introducer and configured to perform a measurement during the non-fluoroscopic transseptal procedure. In this system, the transducer may be embedded on the outer surface of the introducer, or embedded on the inner surface of the introducer, or embedded within the introducer. The transducer may be a ring transducer or a circular transducer. The measurement is based on a plurality of ultrasonic pulses transmitted from the transducer, and the measurement determines a location of the catheter and/or a puncture location. In another embodiment, the transducer is embedded on a needle instead of an introducer.

15 Claims, 6 Drawing Sheets

(51) Int. Cl.
  *A61B 34/20* (2016.01)
  *A61B 90/00* (2016.01)
  *A61B 8/08* (2006.01)
  *A61B 8/12* (2006.01)
  *A61B 5/287* (2021.01)
  *A61B 18/14* (2006.01)
  *A61B 17/00* (2006.01)
  *A61B 18/00* (2006.01)

(52) U.S. Cl.
  CPC ............... *A61B 2034/2051* (2016.02); *A61B 2090/3782* (2016.02)

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 5,944,022 A | 8/1999 | Nardella et al. |
| 5,983,126 A | 11/1999 | Wittkampf |
| 6,102,867 A | 8/2000 | Dietz et al. |
| 6,172,499 B1 | 1/2001 | Ashe |
| 6,177,792 B1 | 1/2001 | Govari et al. |
| 6,266,551 B1 | 7/2001 | Osadchy et al. |
| 6,456,864 B1 | 9/2002 | Swanson et al. |
| 6,690,693 B1 | 2/2004 | Crowder |
| 6,788,967 B2 | 9/2004 | Ben-Haim et al. |
| 7,011,647 B2 | 3/2006 | Purdy et al. |
| 7,815,577 B2 | 10/2010 | Krishnan |
| 8,088,101 B2 * | 1/2012 | Chang ............... A61B 34/20 604/96.01 |
| 8,709,008 B2 | 4/2014 | Willis et al. |
| 9,545,263 B2 | 1/2017 | Lenihan et al. |
| 10,111,645 B2 | 10/2018 | Fearnot et al. |
| 2004/0073110 A1* | 4/2004 | Stewart ............... A61B 8/0883 600/437 |
| 2005/0234436 A1* | 10/2005 | Baxter ............... A61B 18/24 606/14 |
| 2007/0293724 A1* | 12/2007 | Saadat ............... A61B 1/00085 600/156 |
| 2008/0045936 A1* | 2/2008 | Vaska ............... A61B 17/22012 606/27 |
| 2009/0093806 A1 | 4/2009 | Govari et al. |
| 2009/0138007 A1 | 5/2009 | Govari et al. |
| 2010/0168777 A1* | 7/2010 | Stangenes ............... A61B 17/00234 606/185 |
| 2010/0249562 A1 | 9/2010 | Zhang et al. |
| 2010/0305451 A1 | 12/2010 | Kim et al. |
| 2011/0098572 A1 | 4/2011 | Chen et al. |
| 2012/0089022 A1* | 4/2012 | House ............... A61B 8/0883 600/439 |
| 2012/0197113 A1* | 8/2012 | Courtney ............... A61B 8/445 600/427 |
| 2013/0172758 A1* | 7/2013 | de Marchena ......... A61B 8/445 600/464 |
| 2014/0024945 A1 | 1/2014 | Mung et al. |

OTHER PUBLICATIONS

Japanese Office Action dated Jun. 7, 2022 for Japanese Patent Application No. 2020-513761.

\* cited by examiner

METHOD AND APPARATUS FOR PERFORMING NON-FLUOROSCOPIC TRANSSEPTAL PROCEDURE

SUMMARY

A system of performing a non-fluoroscopic transseptal procedure may comprise a catheter and a device comprising a sheath, an introducer, a needle and a transducer embedded on the introducer and configured to perform a measurement during the non-fluoroscopic transseptal procedure. The ultrasound transducer may enable easier and more precise navigation.

The transducer may be embedded on the outer surface of the introducer, embedded on the inner surface of the introducer, or embedded within the introducer. In one embodiment, the transducer is either a ring transducer; in another embodiment, the transducer is a circular transducer. In one embodiment, the transducer has a diameter between 0.1 mm and 2.0 mm. In one embodiment, the measurement is based on a plurality of ultrasonic pulses transmitted from the transducer, and the measurement determines a location of the catheter. In one embodiment, the measurement further determines a puncture location.

In one embodiment, the transducer may be embedded on the needle instead of the introducer.

The method for performing a non-fluoroscopic transseptal procedure may comprise steps of transmitting an ultrasound signal from a transducer in a device, receiving the ultrasound signal, performing a measurement based on the ultrasound signal and determining a position of a catheter using the measurement, wherein the device further comprises a sheath, an introducer and a needle.

In one embodiment, the ultrasound signal of the method is a plurality of ultrasonic pulses. In one embodiment, the measurement determines a thickness of a tissue. In one embodiment, the thickness of the tissue may determine a puncture location. In one embodiment, the measurement determines a distance to a tissue.

BRIEF DESCRIPTION OF THE DRAWINGS

The present embodiments are illustrated by way of example, and not by way of limitation, in the figures of the accompanying drawings in which.

DETAILED DESCRIPTION OF THE PREFERRED EMBODIMENTS

Documents incorporated by reference in the present patent application may include terms that are defined in a manner that conflicts with the definitions made explicitly or implicitly in the present specification. In the event of any conflicts, the definitions in the present specification should be considered to be controlling.

Figure 1:
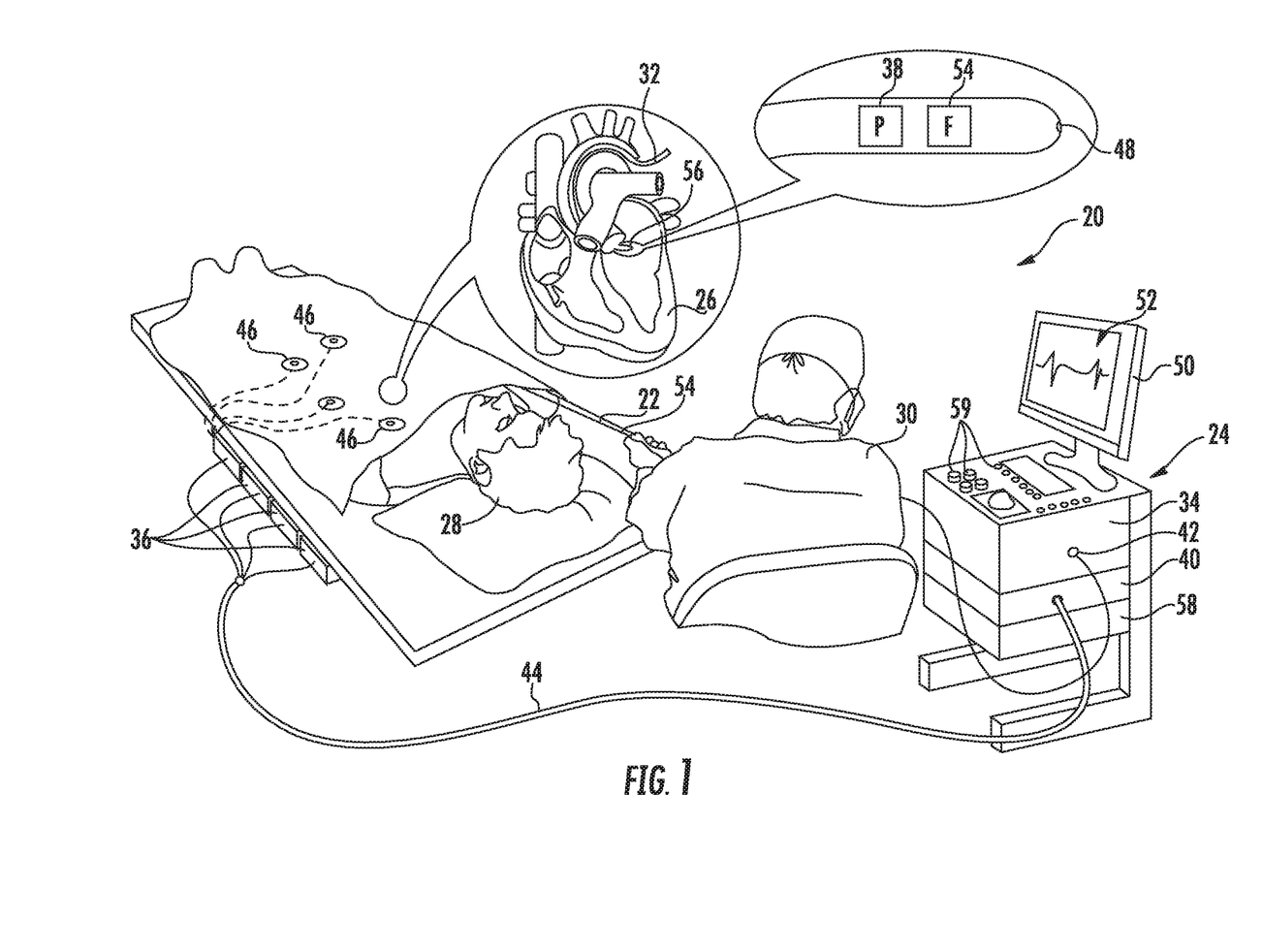
FIG. 1 is an example schematic, pictorial illustration of a medical system for performing a non-fluoroscopic transseptal procedure.

FIG. 1 is an illustration of an example medical system 20 that may be used to generate and display information 52 during a medical procedure. The system 20 may include a probe 22, such as an intracardiac catheter, and a console 24. As described herein, it may be understood that the probe 22 is used for diagnostic or therapeutic treatment, such as for example, mapping electrical potentials in a heart 26 of a patient 28 or performing an ablation procedure. Alternatively, the probe 22 may be used, mutatis mutandis, for other therapeutic and/or diagnostic purposes in the heart, lungs, or in other body organs and ear, nose, and throat (ENT) procedures.

An operator 30 may insert the probe 22 into the vascular system of the patient 28 so that a distal end 32 of the probe 22 enters a chamber of the patient's heart 26. The console 24 may use magnetic position sensing to determine position coordinates of the distal end 32 inside the heart 26. To determine the position coordinates, a driver circuit 34 in the console 24 may drive field generators 36 to generate magnetic fields within the body of the patient 28. The field generators 36 may include coils that may be placed below the torso of the patient 28 at known positions external to the patient 28. These coils may generate magnetic fields in a predefined working volume that contains the heart 26.

A location sensor 38 within the distal end 32 of probe 22 may generate electrical signals in response to these magnetic fields. A signal processor 40 may process these signals in order to determine the position coordinates of the distal end 32, including both location and orientation coordinates. The method of position sensing described hereinabove is implemented in the CARTO™ mapping system produced by Biosense Webster Inc., of Diamond Bar, Calif., and is described in detail in the patents and the patent applications cited herein.

The location sensor 38 may transmit a signal to the console 24 that is indicative of the location coordinates of the distal end 32. The location sensor 38 may include one or more miniature coils, and typically may include multiple coils oriented along different axes. Alternatively, the location sensor 38 may comprise either another type of magnetic sensor, or position transducers of other types, such as impedance-based or ultrasonic location sensors. Although FIG. 1 shows the probe 22 with a single location sensor 38, embodiments of the present invention may utilize probes without a location sensor 38 and probes with more than one location sensor 38.

The probe 22 may also include a force sensor 54 contained within the distal end 32. The force sensor 54 may measure a force applied by the distal end 32 to the endocardial tissue of the heart 26 and generating a signal that is sent to the console 24. The force sensor 54 may include a magnetic field transmitter and a receiver connected by a spring in the distal end 32, and may generate an indication of the force based on measuring a deflection of the spring. Further details of this type of probe and force sensor are described in U.S. Patent Application Publications 2009/0093806 and 2009/0138007, and are incorporated herein by reference as if fully set forth. Alternatively, the distal end 32 may include another type of force sensor that may use, for example, fiber optics or impedance measurements.

The probe 22 may include an electrode 48 coupled to the distal end 32 and configured to function as an impedance-based position transducer. Additionally or alternatively, the electrode 48 may be configured to measure a certain physiological property, for example the local surface electrical potential of the cardiac tissue at one or more of the multiple locations. The electrode 48 may be configured to apply radio frequency (RF) energy to ablate endocardial tissue in the heart 26.

Although the example medical system 20 may be configured to measure the position of the distal end 32 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126, 6,456,864 and 5,944,022, and are incorporated herein by reference as if fully set forth.

The signal processor 40 may be included in a general-purpose computer, with a suitable front end and interface circuits for receiving signals from the probe 22 and controlling the other components of the console 24. The signal processor 40 may be programmed, using software, to carry out the functions that are described herein. The software may be downloaded to the console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example of FIG. 1, the console 24 may also be connected by a cable 44 to external sensors 46. The external sensors 46 may include body surface electrodes and/or position sensors that may be attached to the patient's skin using, for example, adhesive patches. The body surface electrodes may detect electrical impulses generated by the polarization and depolarization of cardiac tissue. The position sensors may use advanced catheter location and/or magnetic location sensors to locate the probe 22 during use. Although not shown in FIG. 1, the external sensors 46 may be embedded in a vest that is configured to be worn by the patient 28. The external sensors 46 may help identify and track the respiration cycle of the patient 28. The external sensors 46 may transmit information to the console 24 via the cable 44.

Additionally, or alternatively, the probe 22, and the external sensors 46 may communicate with the console 24 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth, or acoustic transmissions.

The probe 22 may be equipped with a wireless digital interface that may communicate with a corresponding input/output (I/O) interface 42 in the console 24. The wireless digital interface and the I/O interface 42 may operate in accordance with any suitable wireless communication standard that is known in the art, such as IR, RF, Bluetooth, one of the IEEE 802.11 families of standards, or the HiperLAN standard. The external sensors 46 may include one or more wireless sensor nodes integrated on a flexible substrate. The one or more wireless sensor nodes may include a wireless transmit/receive unit (WTRU) enabling local digital signal processing, a radio link, and a power supply such as miniaturized rechargeable battery.

The I/O interface 42 may enable the console 24 to interact with the probe 22 and the external sensors 46. Based on the electrical impulses received from the external sensors 46 and signals received from the probe 22 via the I/O interface 42 and other components of the medical system 20, the signal processor 40 may generate the information 52, which may be shown on a display 50. The information 52 may be in the form of a chart, a photograph, a video, or the like.

During the diagnostic treatment, the signal processor 40 may present the information 52 and may store data representing the information 52 in a memory 58. The memory 58 may include any suitable volatile and/or non-volatile memory, such as random access memory or a hard disk drive. The operator 30 may be able to manipulate the information 52 using one or more input devices 59. Alternatively, the medical system 20 may include a second operator that manipulates the console 24 while the operator 30 manipulates the probe 22.

One of a several number of options for treating cardiac arrhythmias may be an interventional catheter based procedure. An interventional catheter based procedure may involve a technique referred to as cardiac ablation. In such a procedure, a catheter is usually advanced from the groin area of a patient into the heart. Once in place, radio frequency (RF) energy may be delivered through the catheter to a specific location with the goal of re-establishing proper heart conduction. In some cases, the physician may require access to the left side of the heart to treat arrhythmias that originate in the left atrium or left ventricle.

To gain access to the left side of the heart, a transseptal puncture is required. The catheter being used enters the right atrium via either the inferior or superior vena cava, after being inserted into either a femoral or brachiocephalic vein, respectively. The catheter is pushed up against the fossa ovalis, and a hole through the septum is created. The fossa ovalis is a depression in the right atrium of the heart, at the level of the interatrial septum, the wall between right and left atrium. The fossa ovalis is the remnant of a thin fibrous sheet that covered the foramen ovale during fetal development. Location of the fossa ovalis is usually determined through the use of fluoroscopy. Once the transseptal puncture is performed, an electrophysiology catheter may be advanced into the left atrium to treat the arrhythmia.

Figure 2:
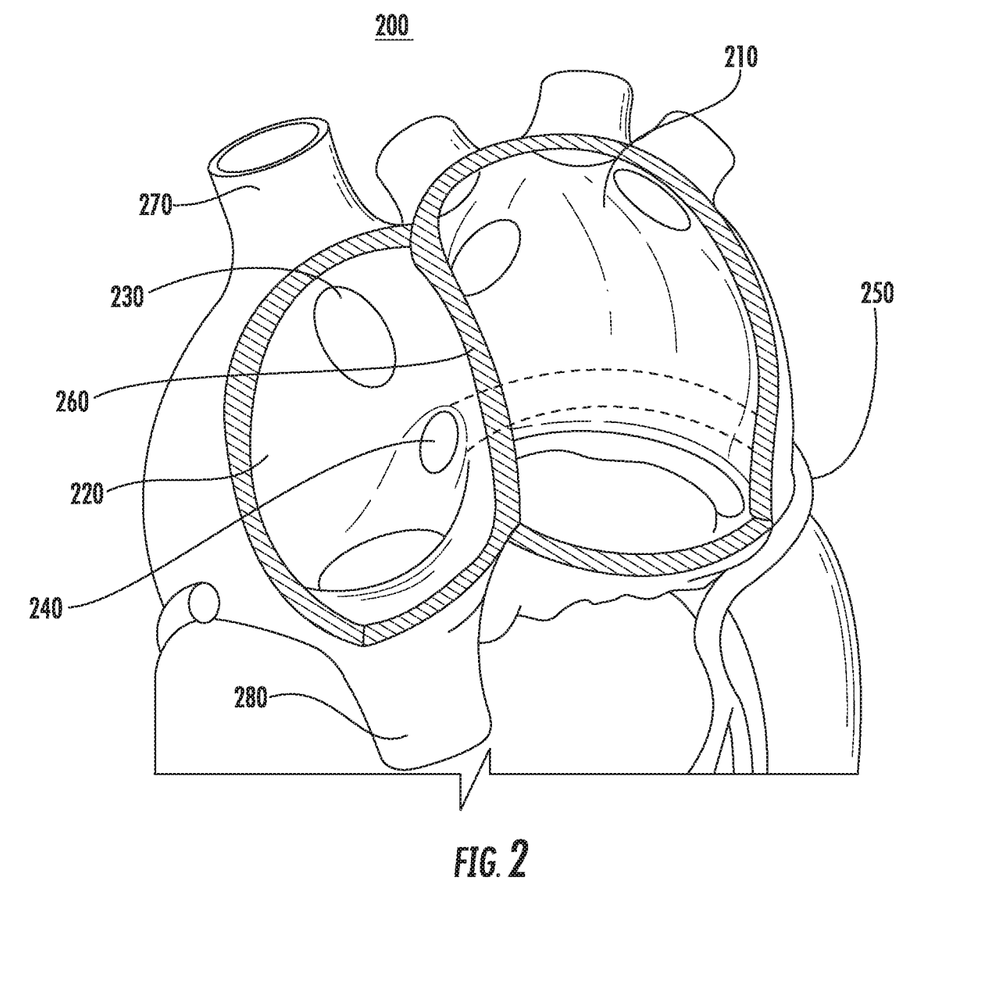
FIG. 2 is a diagram of an anatomic anterior perspective view of a heart.

FIG. 2 is a diagram of an anatomic anterior perspective view of a heart 200. The left atrium 210 and right atrium 220 are shown with portions broken away and in section to show the interior of the heart chambers and associated structures, such as the fossa ovalis 230, coronary sinus 240, and the great cardiac vein 250. As shown in FIG. 2, the left atrium 210 and the right atrium 220 are separated by the interatrial septum 260. In order to perform a transseptal puncture, a physician may insert a catheter into the right atrium 220 via the superior vena cava 270 or the inferior vena cava 280.

Figure 3:
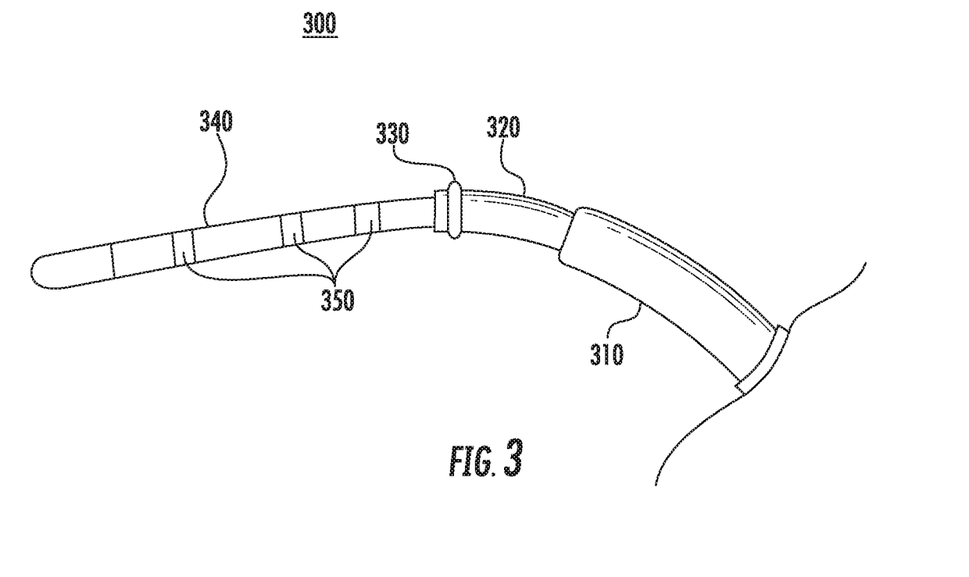
FIG. 3 is a diagram of an example catheter that includes a ring transducer on an introducer.

FIG. 3 is a diagram of an example catheter 300, which serves as an example probe 22 in one embodiment. The catheter 300 includes a sheath 310, an introducer 320, a ring transducer 330, and a distal end 340. In this example, the distal end 340 may include one or more electrodes 350. The introducer 320 may be used to puncture the fossa ovalis and may include a ring transducer 330. The transducer 330 may have a diameter that can be from 0.5 mm to 2.0 mm; its thickness may be between 0.1 mm and 1.5 mm. The transducer 330 can be placed at the distal end of the introducer facing with angles that can range from 0 to 90 degrees. Accordingly, the transducer 330 may face totally forward or totally to the side or somewhere in between. The ring transducer 330 may be embedded in the introducer 320. In another example, the ring transducer 330 may be located on the outer surface of the introducer 320. In yet another example, the ring transducer 330 may be located on the inner surface of the introducer 320.

The ring transducer 330 may use ultrasound to detect a depression in the tissue of the right atrium and indicate the area of the fossa ovalis during a non-fluoroscopic transseptal procedure. For example, the ring transducer 330 may transmit and receive ultrasonic pulses to measure the distance to the tissue. A pulse signal is generated from the transducer 330 and the system 20 waits to receive the returned pulses. From the return pulses that are generated by the different structures that the pulse is passing through the thickness of the tissue can be measured by measuring the time interval between relevant returning pulses. The measured distance may be used to determine the thickness of the tissue without the need for fluoroscopy. During the procedure, the operator may receive an audible, visual, or haptic indication that a depression in the wall thickness is detected and indicating that the fossa ovalis has been reached. Once the fossa ovalis has been reached, the operator may puncture the fossa ovalis with the introducer 320 and proceed with the transseptal procedure.

Figure 4:
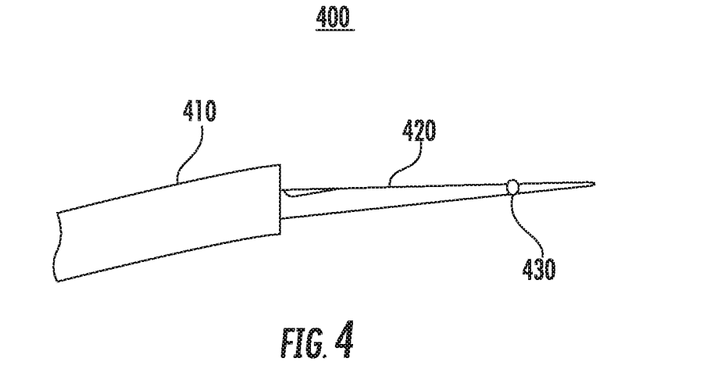
FIG. 4 is a diagram of an example catheter that includes a ring transducer on a needle.

FIG. 4 is a diagram of another example catheter 400 which serves as another example probe 22 in another embodiment. The catheter 400 includes a ring transducer on a needle. Note that the invention is not limited to a ring transducer. Other transducers such as a circular transducer and/or a transducer that is a portion of a ring may be used. The catheter 400 may include a sheath 410 and a needle 420. The sheath 410 and needle 420 typically are part of the same device used for the transseptal procedure while the catheter 400 may be a separate device. The needle 420 may be used to puncture the fossa ovalis and may include a ring transducer 430. The ring transducer 430 may vary depending on the sheath size (introducer size and/or needle); typical sheath dimensions are diameters of 7 Fr to 15 Fr. The dimensions of the needle 420 may be smaller, going down to 0.8 mm diameter. The ring thickness can vary from 0.1 mm to 1.5 mm. The ring transducer 430 may be embedded in the needle 420. In another example, the ring transducer 430 may be located on the outer surface of the needle 420. In yet another example, the ring transducer 430 may be located on the inner surface of the needle 420.

The ring transducer 430 may use ultrasound to detect a depression in the tissue of the right atrium and indicate the area of the fossa ovalis during a non-fluoroscopic transseptal procedure. For example, the ring transducer 430 may transmit and receive ultrasonic pulses to measure the distance to the tissue as performed in ultrasound applications. The measured distance may be used to determine the thickness of the tissue without the need for fluoroscopy. During the procedure, the operator may receive an audible, visual, or haptic indication that a depression in the wall thickness is detected and indicating that the fossa ovalis has been reached. Once the fossa ovalis has been reached, the operator may puncture the fossa ovalis with the needle 420 and proceed with the transseptal procedure.

Figure 5:
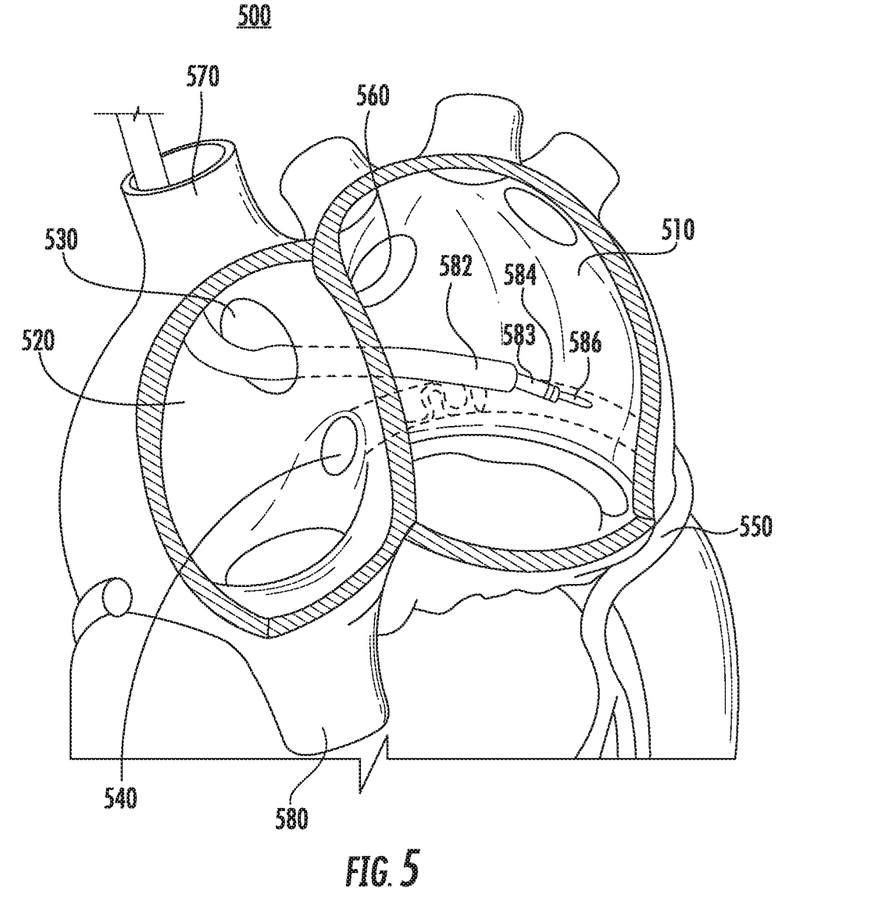
FIG. 5 is an anatomic view depicting an example catheter penetrating the fossa ovalis and entering the left atrium.

FIG. 5 is an anatomic view of a heart 500 depicting a probe 22, such as a catheter 586, penetrating the fossa ovalis and entering the left atrium. The left atrium 510 and right atrium 520 are shown with portions broken away and in section to show the interior of the heart chambers and associated structures, such as the fossa ovalis 530, coronary sinus 540, and the great cardiac vein 550. As shown in FIG. 5, the left atrium 510 and the right atrium 520 are separated by the interatrial septum 560. In order to perform a non-fluoroscopic transseptal puncture, a physician may insert a catheter 586 into the right atrium 520 via the superior vena cava 570 or the inferior vena cava 580.

In this example, the catheter 586 includes a sheath 582 and an introducer 583. The introducer 583 may include a ring transducer 584. The introducer 583 may be used to puncture the fossa ovalis and may include a ring transducer 584. The ring transducer 584 may be embedded in the introducer 583. In another example, the ring transducer 584 may be located on the outer surface of the introducer 583. In yet another example, the ring transducer 584 may be located on the inner surface of the introducer 583.

The ring transducer 584 may use ultrasound to detect a depression in the tissue of the right atrium 520 and indicate the area of the fossa ovalis 530. For example, the ring transducer 584 may transmit and receive ultrasonic pulses to measure the distance to the tissue. The measured distance may be used to determine the thickness of the tissue without the need for fluoroscopy. During the procedure, the operator may receive an audible, visual, or haptic indication that a depression in the wall thickness is detected and indicating that the fossa ovalis 530 has been reached. Once the fossa ovalis 530 has been reached, the operator may puncture the fossa ovalis with the introducer 583 and proceed with the non-fluoroscopic transseptal procedure.

Figure 6:
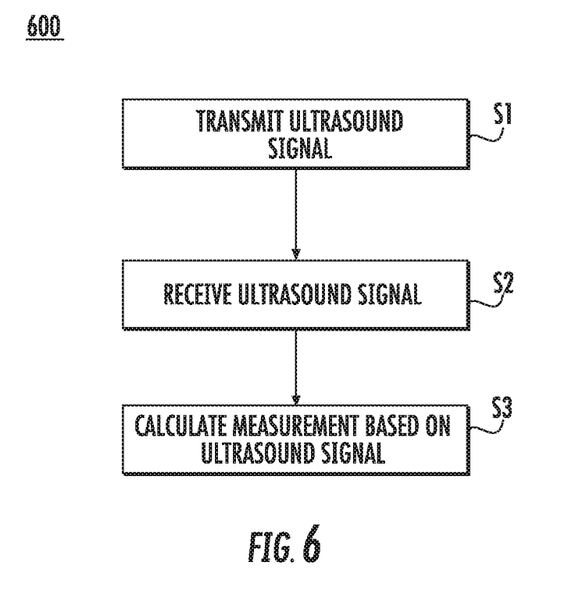
FIG. 6 is a diagram of an example method for performing a non-fluoroscopic transseptal procedure.

FIG. 6 is a diagram of an example method 600 for performing a non-fluoroscopic transseptal procedure. In this example, in step S1, a ring transducer on an introducer or a needle may transmit ultrasonic signals. The ultrasonic signals may be in the form of ultrasonic pulses.

In step S2, the ring transducer may receive ultrasonic signals.

In step S3, the system may calculate a measurement based on the received ultrasonic signals. This measurement may be used to determine the thickness of the tissue. The ultrasonic signals may also be used to determine the position of the catheter and aid the operator in navigating the catheter to the appropriate target. Alternatively, or in addition to calculating the thickness of the tissue, the system may calculate the distance of the tissue from the catheter based on the received ultrasonic signals.

Figure 7:
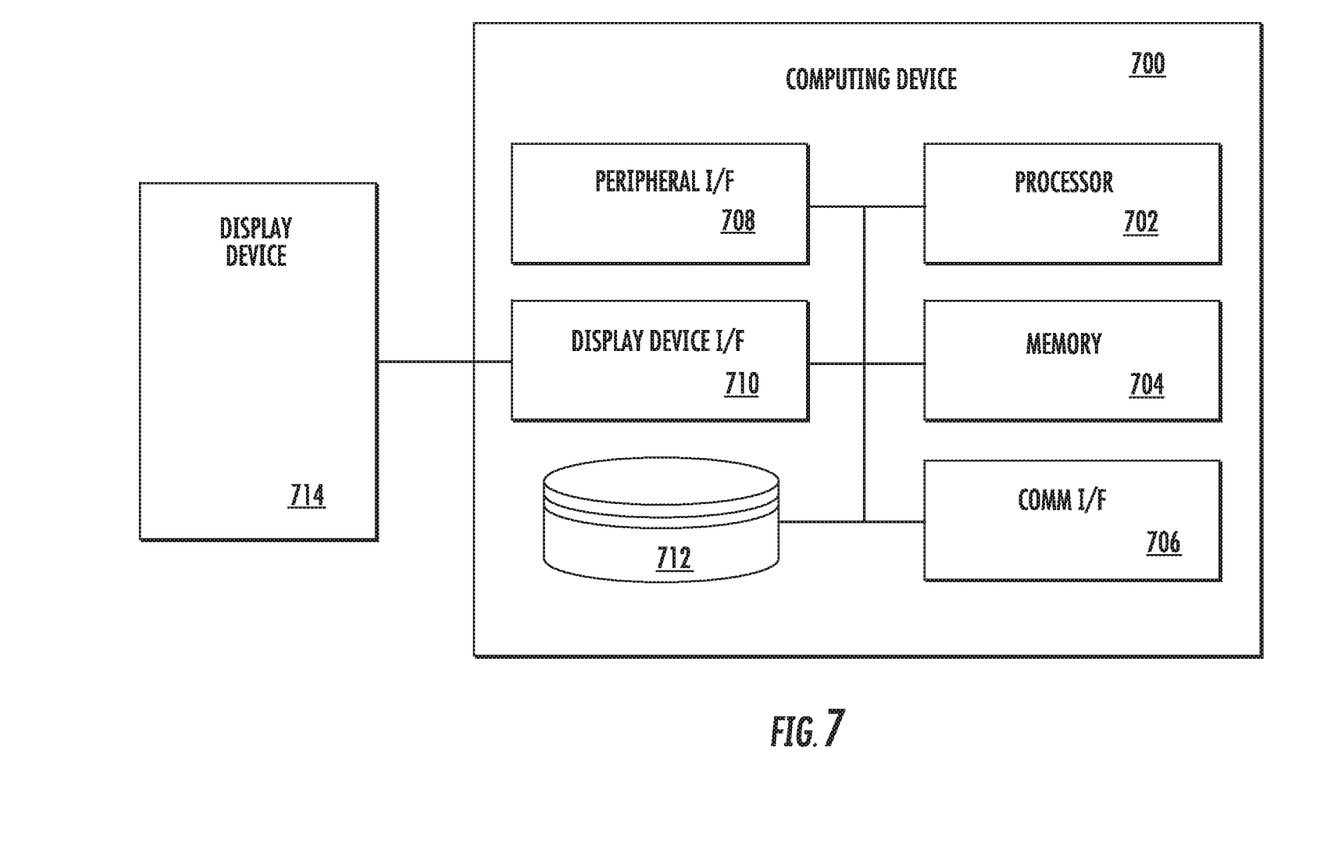
FIG. 7 is a diagram of an example computing device that may be used to implement features of the elements described above.

FIG. 7 is a diagram of an example computing device 700 that may be used to implement features of the elements described above. The computing device 700 may be part of the console 24 as described above with reference to FIG. 1. The computing device 700 may include a processor 702, a memory device 704, a communication interface 706, a peripheral device interface 708, a display device interface 710, and a storage device 712. FIG. 7 also shows a display device 714, which may be coupled to or included within the computing device 700.

The memory device 704 may be or include a device such as a Dynamic Random Access Memory (D-RAM), Static RAM (S-RAM), or other RAM or a flash memory. The storage device 712 may be or include a hard disk, a magneto-optical medium, an optical medium such as a CD-ROM, a digital versatile disk (DVDs), or Blu-Ray disc (BD), or other type of device for electronic data storage.

The communication interface 706 may be, for example, a communications port, a wired transceiver, a wireless transceiver, and/or a network card. The communication interface 706 may be capable of communicating using technologies such as Ethernet, fiber optics, microwave, xDSL (Digital Subscriber Line), Wireless Local Area Network (WLAN) technology, wireless cellular technology, and/or any other appropriate technology.

The peripheral device interface 708 may be an interface configured to communicate with one or more peripheral devices. The peripheral device interface 708 may operate using a technology such as Universal Serial Bus (USB), PS/2, Bluetooth, infrared, serial port, parallel port, and/or other appropriate technology. The peripheral device interface 708 may, for example, receive input data from an input device such as a keyboard, a mouse, a trackball, a touch screen, a touch pad, a stylus pad, and/or other device. Alternatively or additionally, the peripheral device interface 708 may communicate output data to a printer that is attached to the computing device 700 via the peripheral device interface 708.

The display device interface 710 may be an interface configured to communicate data to display device 714. The display device 714 may be, for example, a monitor or television display, a plasma display, a liquid crystal display (LCD), and/or a display based on a technology such as front or rear projection, light emitting diodes (LEDs), organic light-emitting diodes (OLEDs), or Digital Light Processing (DLP). The display device interface 710 may operate using technology such as Video Graphics Array (VGA), Super VGA (S-VGA), Digital Visual Interface (DVI), High-Definition Multimedia Interface (HDMI), or other appropriate technology. The display device interface 710 may communicate display data from the processor 702 to the display device 714 for display by the display device 714. As shown in FIG. 7, the display device 714 may be external to the computing device 700, and coupled to the computing device 700 via the display device interface 710. Alternatively, the display device 714 may be included in the computing device 700.

An instance of the computing device 700 of FIG. 6 may be configured to perform any feature or any combination of features described above. In such an instance, the memory device 704 and/or the storage device 712 may store instructions which, when executed by the processor 702, cause the processor 702 to perform any feature or any combination of features described above. Alternatively or additionally, in such an instance, each or any of the features described above may be performed by the processor 702 in conjunction with the memory device 704, communication interface 706, peripheral device interface 708, display device interface 710, and/or storage device 712.

Although FIG. 7 shows that the computing device 700 includes a single processor 702, single memory device 704, single communication interface 706, single peripheral device interface 708, single display device interface 710, and single storage device 712, the computing device may include multiples of each or any combination of these components 702, 704, 706, 708, 710, 712, and may be configured to perform, mutatis mutandis, analogous functionality to that described above.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A catheter device for performing a non-fluoroscopic transseptal procedure, the catheter device comprising:
    a sheath;
    an introducer configured to puncture tissue; and
    an ultrasonic ring transducer having an inner surface disposed circumferentially on an outer surface of the introducer and configured to perform a measurement of the thickness of the tissue during the non-fluoroscopic transseptal procedure;
    a distal end portion, extending a length between the introducer and a tip; and
    a plurality of electrodes disposed around the distal end portion at different locations along the length of the distal end portion.

2. The catheter device of claim 1, wherein the transducer has a diameter between 0.1 mm and 2.0 mm.

3. The catheter device of claim 1, wherein the measurement is based on a plurality of ultrasonic pulses transmitted from the transducer, and the measurement determines a location of the catheter.

4. The catheter device of claim 3, wherein the measurement further determines a puncture location.

5. A system for performing a non-fluoroscopic transseptal procedure, the device comprising:
    a catheter; and
    a device comprising:
        a sheath;
        an introducer; and
        a needle having a transducer embedded on an outer surface of the needle, the transducer configured to perform a measurement of the thickness of tissue during the non-fluoroscopic transseptal procedure.

6. The device of claim 5, wherein the measurement is based on a plurality of ultrasonic pulses transmitted from the transducer, and the measurement determines a location of the catheter and a puncture location.

7. The device of claim 5, wherein the transducer is one of a ring transducer or a circular transducer.

8. The device of claim 5, wherein the transducer has a diameter between 0.1 mm and 2.0 mm.

9. A method for performing a non-fluoroscopic transseptal procedure, comprising steps of:
    transmitting an ultrasound signal from a transducer in a device;
    receiving the ultrasound signal;
    performing a measurement of the thickness of tissue based on the ultrasound signal; and
    determining a position of a catheter using the measurement;
    wherein the device further comprises a sheath, an introducer and a needle,
    wherein the transducer is one of: embedded on the outer surface of the introducer, embedded on the inner surface of the introducer, or embedded within the introducer.

10. The method of claim 9, wherein the ultrasound signal is a plurality of ultrasonic pulses.

11. The method of claim 9, wherein the measurement determines a thickness of a tissue.

12. The method of claim 9, wherein the thickness of the tissue is used to determine a puncture location.

13. The method of claim 9, wherein the measurement determines a distance to a tissue.

14. The method of claim 9, wherein the transducer is one of a ring transducer or a circular transducer.

15. A catheter device for performing a non-fluoroscopic transseptal procedure, the catheter device comprising:
   a sheath;
   an introducer configured to puncture tissue; and
   an ultrasonic ring transducer embedded on an outer surface of the introducer and configured to perform a measurement of the thickness of the tissue during the non-fluoroscopic transseptal procedure.

* * * * *

UNITED STATES PATENT AND TRADEMARK OFFICE
CERTIFICATE OF CORRECTION

| | |
|---|---|
| PATENT NO. | : 11,583,249 B2 |
| APPLICATION NO. | : 15/698758 |
| DATED | : February 21, 2023 |
| INVENTOR(S) | : Andres Claudio Altmann |

It is certified that error appears in the above-identified patent and that said Letters Patent is hereby corrected as shown below:

In the Specification
In Column 1, Line 17, delete "either a" and insert -- a --, therefor.

In the Claims
In Column 8, Line 12, in Claim 1, delete "tissue; and" and insert -- tissue; --, therefor.
In Column 8, Line 59, in Claim 9, delete "needle," and insert -- needle; --, therefor.

Signed and Sealed this
Twelfth Day of September, 2023

Katherine Kelly Vidal
*Director of the United States Patent and Trademark Office*